United States Patent [19]

Herrmann

[11] 4,326,078
[45] Apr. 20, 1982

[54] PROCESS FOR PREPARATION OF HYDRAZOBENZENES BY CATALYTIC HYDROGENATION OF NITROBENZENES

[75] Inventor: Hans-Joachim Herrmann, Troisdorf, Fed. Rep. of Germany

[73] Assignee: Dynamit Nobel Aktiengesellschaft, Troisdorf, Fed. Rep. of Germany

[21] Appl. No.: 60,562

[22] Filed: Jul. 25, 1979

[30] Foreign Application Priority Data

Jul. 31, 1978 [DE] Fed. Rep. of Germany ....... 2833605

[51] Int. Cl.$^3$ ............................................. C07C 85/24
[52] U.S. Cl. .................................... 564/312; 260/143; 564/309
[58] Field of Search ......................... 260/569; 564/312

[56] References Cited

U.S. PATENT DOCUMENTS 2,519,673  8/1950  Lecher et al. ........................ 260/569
2,765,301  10/1956  Cashion ........................... 260/569 X
3,063,980  11/1962  Bloom et al. ..................... 260/569 X
3,156,724  11/1964  Werner et al. ...................... 260/569

Primary Examiner—Robert V. Hines
Attorney, Agent, or Firm—Sprung, Felfe, Horn, Lynch & Kramer

[57] ABSTRACT

In a process for the hydrogenation of nitrobenzene with hydrogen to hydrazobenzene at temperatures ranging from 40° to 110° C. in the presence of a precious metal catalyst, an aqueous alkaline solution and an organic solvent, the reaction mixture being maintained in turbulent motion, the improvement wherein said nitrobenzene is o-, m- or p-chloronitrobenzene, the reaction is carried out in an organic solvent in which the dichlorohydrazobenzene being formed is readily soluble when warm and difficultly soluble when cold, and that the precious metal catalyst is used in such amount that the weight ratio of chloronitrobenzene used to precious metal catalyst is in the range 1:0.00005–less than 0.0002.

19 Claims, No Drawings

PROCESS FOR PREPARATION OF HYDRAZOBENZENES BY CATALYTIC HYDROGENATION OF NITROBENZENES

BACKGROUND OF THE INVENTION

1. Field of the Invention

The invention has as its object a process for the hydrogenation of nitrobenzene with hydrogen to hydrazobenzene at temperatures ranging from 40° to 110° C. in the presence of a precious metal catalyst and preferably of a co-catalyst, and in the presence of an aqueous alkaline solution and of an organic solvent, the reaction mixture being maintained in turbulent motion, wherein o-, m- or p-chloronitrobenzene is used as nitrobenzene, the reaction is carried out in an organic solvent in which the dichlorohydrazobenzene is readily soluble when warm and difficultly soluble when cold, and that the precious metal catalyst is employed in such amount that the weight ratio of nitrobenzene to precious metal catalyst used is in the range 1:0.00005–less than 0.0002, and preferably between 1:0.00005 to less than 0.0001.

2. Discussion of the Prior Art

It is known to prepare hydrazobenzenes, starting from the nitro stage, by reduction with zinc and alkali. (Alexeyev, Zeitschrift für Chemie, 1868, 497). Working with zinc, which entails many drawbacks, may be avoided by the use of other reducing agents. However, the reducing agents used, such as dextrose (U.S. Pat. No. 2,794,047), formaldehyde (U.S. Pat. No. 2,794,046), hydrazine hydrate (German patent application DAS No. 2,609,530), sodium sulfide (German patent application DOS No. 2,546,656) or sodium hydrogen sulfide (Belgian Pat. No. 832,268), iron and acid (German patent application DOS No. 2,535,045), and sodium amalgam (German Pat. No. 1,668,898), are difficult to handle technically and, in addition, usually require specially produced azoxybenzenes as starting materials.

Processes for the production of 2,2′ or 3,3′-dichlorohydrazobenzene, respectively, are described in U.S. Pat. No. 3,205,217, German patent application DAS No. 2,609,530 and U.S. Pat. No. 3,156,724, for example. In these prior-art processes, the reduction is carried out with hydrogen and a catalyst. While these hydrogenation processes are easier to handle than the processes described above, they have a number of serious drawbacks. In U.S. Pat. No. 3,205,217, for example, a cobalt-cyanide complex is proposed as catalyst. Working with cyanides calls for extensive safety measures, especially in operating on the industrial scale. A further disadvantage is that this process results in a mixture of different reaction products, which complicates any subsequent purification operations.

In the process described in German patent application DAS No. 2,609,530 (examples 4 and 5), specially produced azoxybenzenes are used. This two-stage procedure makes the process complicated. Another drawback is that relatively large amounts of Raney nickel are required as catalyst.

U.S. Pat. No. 3,156,724 describes a process for the preparation of 2,2′-dichlorohydrazobenzene in which o-chloronitrobenzene is hydrogenated with hydrogen at elevated pressure and at temperatures ranging from 40° to 100° C. in the presence of a palladium or platinum catalyst and of a naphthaquinone as cocatalyst in an aqueous alkaline medium, and preferably in the presence of a solvent which dissolves both the starting product and the end product. Proposed solvents are aromatic hydrocarbons such as toluene, xylene or benzene. The main drawback of this prior-art process is that complex purification operations are required, as pointed out above, to separate the 2,2′-dichlorohydrazobenzene from the undesired byproducts. Even so, only moderately pure 2,2′-dichlorohydrazobenzene is obtained as distillation residue whose melting point differs by a few degrees from that of the pure substance. Another drawback is that relatively large amounts of the catalyst combination are required. (The weight ratio of cocatalyst to o-chloronitrobenzene is to be in the 0.004:1 to 0.008:1 range. The preferred weight ratio of precious-metal catalyst to o-chloronitrobenzene is given as 0.0002:1 to 0.001:1.)

Of the hydrazobenzenes, the dichlorohydrazobenzenes especially are of economic importance. By comparison with unsubstituted hydrazobenzene, they are far less of a health hazard and therefore safer to handle. Of the dichlorohydrazo compounds, 2,2′-dichlorohydrazobenzene particularly is of growing interest as an intermediate product in the manufacture of pigments, e.g., 3,3′-dichlorobenzidine, as described in U.S. Pat. No. 4,075,198. However, 2,2′-dichlorohydrazobenzene is of economic importance also as a starting product in the manufacture of pharmaceutical products.

Dichlorohydrazobenzenes must meet very high purity requirements particularly when they are to be used as intermediate or primary products in the manufacture of pigments since the byproducts, and especially substances formed through over- or underreduction, will interfere with the benzidine or semidine rearrangement which follows and therefore will adversely affect the quality of the pigment. The purification methods employed up to now to separate the by-products formed during the reaction have not been satisfactory in practice. The reason is that it has been necessary to treat the reaction product after separation of the catalyst repeatedly with aqueous mineral acids for extraction of the strongly basic by-products such as aniline and to remove in subsequent further washing operations the excess mineral acid and the salts formed. Despite these repeated washing operations, a purity better than 98 percent usually cannot be achieved. Moreover, there is the risk that an undesirable rearrangement may occur.

It is the object of the present invention to provide a process which commercially is easy to handle, is not afflicted with the drawbacks described above, and furnishes the desired hydrazobenzenes in good quality, especially insofar as purity is concerned, and in good yields.

This object is accomplished by proceeding as specified below.

SUMMARY OF THE INVENTION

In the process of the invention, the nitrobenzenes used as starting materials are hydrogenated with gaseous hydrogen and precious metal catalysts in an aqueous alkaline medium with addition of the organic solvent and with vigorous mixing of all phases until hydrogen absorption ceases, the precious metal catalyst is separated mechanically, for example, by filtration of the warm mixture, the phase containing the dichlorohydrazobenzene is separated while warm, and the dichlorohydrazobenzene is allowed to crystallize out upon cooling and after filtration and drying is recovered as a pure substance. Generally speaking, the reaction product containing the dichlorohydrazobenzene is warmed to a temperature of at least 60° C., preferably 65° to 100° C. Thereafter it is cooled to a temperature of 25° C. or less, preferably 20° to 10° C., to effect crystallization of the dichlorohydrazobenzene product.

Suited for use as organic solvents are aliphatic and/or cycloaliphatic hydrocarbons which are inert to the action of hydrogen under the reaction conditions and are not miscible with water or not miscible therewith in every ratio. Generally straight-chained or branched saturated aliphatic and/or cycloaliphatic hydrocarbons which at the particular reaction temperature (at atmospheric pressure) are present as liquids are preferably used. These include alkanes and cycloalkanes as well as cycloheptane, n-hexane, cyclohexane, n-octane, isooctanes, m-decane, n-dodecane and mixture thereof. Suitable hydrocarbons of that type are, in particular, $C_5$ to $C_{12}$ hydrocarbons.

In addition to or in place of the hydrocarbons, there may be used primary, secondary or tertiary alcohols, and preferably primary monohydric aliphatic or cycloaliphatic alcohols, in particular $C_4$ to $C_8$ alcohols, which under the reaction conditions are inert to hydrogen and which are not miscible with water or not miscible therewith in every ratio. Alkanols and cycloalkanols are preferred.

Depending on the desired reaction temperatures, solvents are preferably used whose vapor pressure at the reaction temperature does not exceed 1 bar.

A further requirement with respect to the solvents to be used is that they must be recoverable by simple means in order that they may be recycled to the reduction process. Particularly well suited are the $C_6$ to $C_{10}$ hydrocarbons with boiling points ranging from 68.7° C. (hexane) to 174.1° C. (decane). However, petroleum fractions such as petroleum ether, light gasoline, heavy gasoline, ligroin and the like are also suited for use as solvents. Preferred cycloaliphatic compounds are the $C_5$ to $C_8$ hydrocarbons. In the process of the invention, n-heptane and/or cyclohexane are preferably used. Of the alcohols named, n-butanol is preferred.

The weight ratio of solvent to nitrobenzene used generally ranges from 0.3:1 to 4:1 and preferably is 1.5:1. However, depending on its solubilizing behavior toward nitrobenzene, which during the hydrogenation must be present in the form of a solution or melt, and toward dichlorohydrazobenzene, which is to crystallize out as the organic phase cools off, said weight ratio may also be above or below that range.

As alkaline media, strong water soluble bases are used, primarily alkali metal hydroxides, and particularly sodium hydroxide or potassium hydroxide or alkaline earth hydroxide, in particular barium hydroxide, possibly also mixtures of these hydroxides. It is advisable that the aqueous alkaline phase have a pH value of at least 12. Sodium hydroxide is preferably used in aqueous solution.

The concentrations of the aqueous solutions used range from 12 to 40 weight percent. The aqueous alkaline solutions are preferably over 20 and up to 40 weight percent solutions in the case of sodium hydroxide, and over 20 and up to 38 weight percent solutions in the case of potassium hydroxide. The reason for this is that it has surprisingly been found that contrary to the teaching of U.S. Pat. No. 3,156,724, column 2, lines 23 to 25, the best results are obtained when over 20 weight percent alkaline solutions are used.

The aqueous solution is preferably used in such amounts that the concentration of the liquor at the start of the reduction has a high value of from 38 to 40 weight percent and at the end of the reduction, after dilution with the water formed in the course of the reaction, ranges from 14 to 27 weight percent, and preferably from 18 to 27 weight percent. With this procedure, less chloroaniline forms.

Generally the weight ratios of the aqueous alkaline solutions used to the nitrobenzenes used will be comprised between 0.2:1 and 2.6:1, and preferably between 0.5:1 and 0.8:1.

For better emulsification of the aqueous and organic phases, small amounts of emulsifiers, such as sulfonic acid esters of long-chain aliphatic alcohols, may be added.

As catalysts, precious-metal catalysts such as palladium, platinum and rhodium are used, individually or in mixture, preferably on an inert carrier such as activated charcoal, alumina, titania or silica gel. Commercial precious metal catalysts usually have a metal content of from 0.5 to 20 weight percent. Catalysts having a precious metal content of from 1 to 5 percent are preferably used. The preferred catalysts are commercially available types with 5 weight percent platinum in reduced form on activated charcoal, with a bulk density of from 250 to 300 g/l, and preferably of about 270 g/l, a particle size distribution between 5 and 60$\mu$ (80 weight percent), and preferably between 5 and 40$\mu$, a specific total surface according to BET of from 700 to 1,000 $m^2/g$, and preferably of about 800 $m^2/g$, a specific metal surface of 15 to 25 $m^2/g$, and preferably of about 20 $m^2/g$, and an ash content of under 0.1 weight percent.

Amounts of precious metal catalyst specified herein are based on the weight of the pure metal. The particle sizes of the precious metal catalysts preferably used generally range from 0 to 60$\mu$.

Preferred are catalysts which can be readily and completely separated from the reaction mixture by mechanical means, for example, by filtration or centrifugation. Such catalysts in particular can readily washed after use, for example, with solvents such as acetone or methanol, and restored to a serviceable condition.

Suited for use as co-catalysts are quinones such as p-benzoquinone, hydroquinone, 1,4-naphthaquinone, 1,4-naphthalenediol, 5,6,7,8-tetrahydronaphthaquinone-1,4, 2,3-dichloronaphthaquinone-1,4 and the like. Preferably used are members of the naphthalene series, particularly 1,4-naphthaquinone.

The weight ratio of the cocatalysts to the nitrobenzene used is comprised between 0.0005:1 and less than 0.002:1, and preferably between 0.0005:1 and 0.0015:1. Without cocatalyst, relatively large amounts of chloroanilines are obtained. In addition, there is the danger that dehalogenation may set in.

The hydrogen pressure may be maintained within wide limits during the reduction. It may range from 0.5 to 30 bars and higher. The preferred operating range is from 6 to 12 bars, the higher pressure being advantageous especially toward the end of the reduction. Operation with rising, and preferably steadily rising, pressure therefore is preferred.

The reaction is carried out in the temperature range from 40° to 110° C., and preferably from 55° to 75° C., where the reaction rate already is sufficiently high and the risk of byproduct formation due to dehalogenation or overreduction is still low. The heat of reaction evolved, which is considerable, is eliminated by cooling so that the temperature of the reaction vessel may remain constant.

It is advantageous to provide as large a mass-transfer surface as possible in the reaction space, for example, an autoclave, by bringing all phases into intimate contact with one another. This may be done by the use of efficient mass-transfer apparatus such as gas spargers, rotary reactors with flow obstacles, nozzles or the like.

A particularly preferred apparatus which may be used in the practice of the invention is described in U.S. patent application Ser. No. 821,422, filed Aug. 3, 1977, and its continuation application Ser. No. 046,522, filed June 7, 1979, both of which applications are assigned to the assignee hereof, the disclosures of which are hereby specifically incorporated herein by reference. Essential components of that hydrogenation apparatus are a temperature controlled reactor, a pump, a spray nozzle of the venturi or water-jet pump type, as well as temperature and pressure regulators. Through a recycling conduit the reaction mixture is pumped back into the reactor through a nozzle together with hydrogen.

The reactor is disposed vertically and is dimensioned so that at least 10 to 20 percent of its volume is available as gas space. The recycling conduit, provided with a pump, runs to the nozzle, which is disposed in the upper portion of the reactor in the area of the gas space and projects into the hydrogen gas space of the reactor. Hydrogen may be fed to the nozzle through a lateral suction pipe to which hydrogen is supplied continuously. On completion of hydrogenation, the reaction mixture is removed from the reactor, preferably under a nitrogen atmosphere, and filtered while hot.

The reaction time usually is 2 to 6 hours. However, it may be longer or shorter, depending on temperature, pressure and amount of catalyst. During that time, the starting product nitrobenzenes substantially convert to the target product hydrazobenzenes through the usually manageable azoxybenzene intermediate stage. The amount of anilines formed through overreduction is relatively small. On completion of the reaction, indicated by a cessation of hydrogen absorption and a subsiding of the evolution of heat, the reaction mixture is filtered while hot or centrifuged for separation of the solids, and particularly of the catalysts. In the next step, the hot aqueous alkaline phase, which usually settles as heavy phase, is separated by draining, for example, from the hot organic phase. The latter is then cooled, for example, in water cooled vessels, with the dichlorohydrazobenzene crystallizing out. On completion of crystallization, the crystalline product is separated from the mother liquor mechanically, for example, by filtration. After drying, preferably under vacuum, the hydrazobenzenes are obtained as pure substances.

In a preferred mode of practice of the process in accordance with the invention, the hydrogenation and the separation of the solids and of the aqueous alkaline solution are carried out in the same or approximately the same temperature range.

In another preferred mode of practice, the nitrobenzene used in the hydrogenation is o-chloronitrobenzene.

The solvent, which constitutes the bulk of the organic mother liquor, may be recovered by distillation and recycled. Any anilines which may have formed during the reduction will be in the residue after the solvent has been distilled off and can be recovered by distillation at elevated temperature and/or under vacuum. The residue then remaining crystallizes on cooling with the addition of solvent and furnishes a second fraction of the hydrazobenzene. The solvent used is preferably the same as that used in the reduction.

The previously separated aqueous alkaline mother liquor is freed from small amounts of dissolved or emulsified solvent by distillation, heated with the addition of activated charcoal, preferably to the boiling point, and preferably with air being bubbled in, with most of the organic material still present then precipitating as a slurry, the liquor being restored to its original concentration by distilling off the water which formed during the reduction. After filtration, a liquor is obtained which may be used about another ten times for reduction.

The process described offers a number of advantages over prior-art processes.

The desired hydrazobenzenes are obtained directly from the nitro stage without there being any need for using separately manufactured intermediate products. The target products are obtained in good yields and high purities. This is a considerable advantage when they are used in the manufacture of benzidines for use in the synthesis of dyes, as the quality of the latter largely depends on the purity of the hydrazobenzenes used. For reduction of the nitrobenzenes, relatively small amounts of precious-metal catalysts are required, and these may be in the easily handled water-moist condition in which they are supplied. They may be recovered and reused either as is or after reprocessing by the manufacturer. Even though only small amounts of catalyst are used, the reaction terminates in a sufficiently short time. All auxiliary substances, and particularly the organic solvent and the aqueous alkali, are recycled after being passed through purification stages, and the only byproduct therefore is reaction water which has been purified by distillation and is ecologically harmless. The process steps are readily controlled, which makes the process easy to handle and therefore reliable in operation.

EXAMPLE 1

630 g m-chloronitrobenzene, 450 g water and 135 g NaOH (corresponding to a 23.1 wt. % aqueous solution), 0.7 g naphthalenediol-1,4, 500 g cyclohexane and 0.7 g palladium on activated charcoal (5% Pd) (the quantitative ratio of palladium metal to m-chloronitrobenzene used being 0.000055:1) are hydrogenated in an autoclave at 65° to 75° C. under a hydrogen pressure of 7 bars and with vigorous stirring. The reduction is completed after 3 to 3½ hours, which is indicated by a cessation of hydrogen absorption. The catalyst is filtered off at 75° to 80° C. and allowed to stand until the two remaining liquid phases have completely separated, the heavy aqueous phase is removed by draining at 75° to 80° C., and the upper phase containing the reduction product is fed to the crystallizer. After cooling to 20° C., the precipitated 3,3'-dichlorohydrazobenzene is filtered off, washed with about 100 g cold cyclohexane until the yellow coloration disappears, and dried under vacuum at 60° C. 477 g 3,3'-dichlorohydrazobenzene with a melting point of 94° C. and a purity of about 99%, as determined by liquid chromatography, is obtained, which corresponds to a yield of 94% of theory. Byproduct m-chloroaniline is formed only in an amount of from 1.3 to 1.4 weight percent.

EXAMPLE 2

210 g p-chloronitrobenzene, 600 g water and 180 g sodium hydroxide (corresponding to a 23.1 wt. % aqueous solution), 0.3 g 2,3-dichloronaphthoquinone-1,4, 350 g n-hexane and 0.40 g platinum on activated charcoal (5% Pt) (the quantitative ratio of platinum metal to p-chloronitrobenzene used being 0.000095:1) are hydrogenated by the use of a gas sparger at a hydrogen pressure of 6 bars and at 60° to 65° C. The reduction is completed after 4 to 5 hours. The procedure set forth in Example 1 is followed, 151 g 4,4'-dichlorohydrazobenzene with a melting point of 120° to 121° C. and a purity of 98.5% being obtained, which corresponds to a yield of 88.5% of theory. The possible byproduct p-chloroaniline is not detectable.

EXAMPLE 3

630 g o-chloronitrobenzene, 615 g water and 185 g sodium hydroxide (corresponding to a 23.1 wt. % aqueous solution), 0.9 g naphthalenediol-1,4, 535 g n-butanol and 1.0 g palladium on alumina (5% Pd) (the quantitative ratio of palladium metal to o-chloronitrobenzene used being 0.00008:1) are hydrogenated at a hydrogen pressure of 6 bars and at 55° to 65° C. for 4 hours and worked up as described in Example 1. 396 g pure 2,2'-dichlorohydrazobenzene of a purity of better than 98% is obtained in a yield of 78% of theory. In addition, 37 g o-chloroaniline is obtained which after the n-butanol has been drawn off is distillable under vacuum and thus may be recovered pure. When the distillation residue is mixed with 65 g n-butanol of 60° C., a second fraction of 61 g 2,2'-dichlorohydrazobenzene of a purity of from 97 to 98% crystallizes out on cooling. The total hydrazobenzene yield thus is 89.8%. In addition, 7.3 wt. % o-chloroaniline is obtained.

EXAMPLE 4

63 kg o-chloronitrobenzene, 31.1 kg water and 13.85 kg of 86.7 wt. % potassium hydroxide (corresponding to a 26.8 wt. % aqueous solution), 65 kg n-heptane, 92 g 1,4-naphthoquinone and 350 g platinum/charcoal (1% Pt) (the quantitative ratio of platinum metal to o-chloronitrobenzene used being 0.000055:1) are hydrogenated in a rotary reactor for 4 hours at a hydrogen pressure of 6 bars and at 55° to 65° C. and then worked up as described in Example 3. Two fractions of 2,2'-dichlorohydrazobenzene of 39 and 7.5 kg, respectively, are obtained, which corresponds to a total hydrazobenzene yield of 91.5% of theory, as well as 3.2 kg o-chloroaniline, which corresponds to 6.3%. The purity of the hydrazobenzene fractions is better than 99% (fraction 1) and better than 98% (fraction 2), as determined by liquid chromatography.

What is claimed is:

1. In a process for the hydrogenation of nitrobenzene with hydrogen to hydrazobenzene at temperatures ranging from 40° to 110° C. in the presence of a precious metal catalyst, an aqueous alkaline solution and an organic solvent, the reaction mixture being maintained in turbulent motion, the improvement wherein said nitrobenzene is o-, m- or p-chloronitrobenzene, the reaction is carried out in the presence of an organic solvent which is an aliphatic or cycloaliphatic hydrocarbon that is not miscible or not miscible in any ratio with water, the precious metal catalyst is used in such amount that the weight ratio of chloronitrobenzene used to precious metal catalyst is in the range 1:0.00005 to less than 0.0002, the aqueous alkaline solution being one wherein the alkali content thereof is greater than 20 weight percent, and the process is carried out in the presence of a quinone as co-catalyst, said quinone co-catalyst being present such that the weight ratio of monochloronitrobenzene to quinone co-catalyst is in the range of 1:0.0005 to less than 0.002.

2. A process according to claim 1 wherein sodium hydroxide or potassium hydroxide is used as the strong base.

3. A process according to claim 2 wherein the aqueous alkaline solution in the case of sodium hydroxide is an over 20 and up to 40 weight percent solution and in the case of potassium hydroxide is over 20 and up to a 38 weight percent solution.

4. A process according to claim 1 wherein the co-catalyst is a quinone of the naphthalene series.

5. A process according to claim 4 wherein the quinone is 1,4-naphthaquinone.

6. A process according to claim 1 wherein the solvent is an aliphatic and/or cycloaliphatic hydrocarbon which under the reaction conditions is inert to the action of hydrogen.

7. A process according to claim 6 wherein the solvent is n-heptane and/or cyclohexane.

8. In a process for the hydrogenation of nitrobenzene with hydrogen to hydrazobenzene at temperatures ranging from 40° to 110° C. in the presence of a precious metal catalyst, an aqueous alkaline solution and an organic solvent, the reaction mixture being maintained in turbulent motion, the improvement wherein said nitrobenzene is o-, m- or p-chloronitrobenzene, the reaction is carried out in the presence of an organic solvent which is an alcohol, the precious metal catalyst is employed in an amount such that the weight ratio of chloronitrobenzene employed to precious metal catalyst is in the range of 1:0.00005 to less than 0.0002, the aqueous alkaline solution employed being one in which the alkali content is greater than 20 weight percent.

9. A process according to claim 8 wherein the solvent is a primary, secondary or tertiary alcohol.

10. A process according to claim 8 wherein the organic solvent is a primary monohydric aliphatic or cycloaliphatic alcohol.

11. A process according to claim 8 wherein said organic solvent is a $C_4$–$C_8$ alcohol.

12. A process according to claim 8 wherein said organic solvent is n-butanol.

13. A process according to claim 1 wherein upon completion of the hydrogenation the solids are mechanically separated while warm and the hydrazobenzene is recovered from the organic phase by crystallization by cooling after the aqueous alkaline phase has been separated from the reaction mixture while warm.

14. A process according to claim 13 wherein the hydrogenation and separation of the solids as well as of the aqueous alkaline solution are carried out in the same or approximately the same temperature range.

15. A process according to claim 14 wherein the hydrogenation and separation of the solids are carried out at a temperature of 60° to 100° C.

16. A process according to claim 1 wherein the nitrobenzene is orthochloronitrobenzene.

17. A process according to claim 1 wherein the nitrobenzene is m-chloronitrobenzene.

18. A process according to claim 1 wherein the weight ratio of chloronitrobenzene to precious metal catalyst is in the range of 1:0.00005 to less than 0.0001.

19. A process according to claim 1 wherein the weight ratio of monochloronitrobenzene to co-catalyst is in the range of 1:0.0005 to 0.0015.

* * * * *